United States Patent [19]
Klauke

[11] 3,931,276
[45] Jan. 6, 1976

[54] 2-CHLORO-TRICHLORO-BENZONITRILES

[75] Inventor: Erich Klauke, Odenthal-Hahnenberg, Germany

[73] Assignee: Bayer Aktiengesellschaft, Leverkusen, Germany

[22] Filed: Mar. 5, 1973

[21] Appl. No.: 338,008

[30] Foreign Application Priority Data
Mar. 23, 1972 Germany............................ 2214058

[52] U.S. Cl. ............... 260/465 G; 71/105; 424/304
[51] Int. Cl.[2]....................................... C07C 121/52
[58] Field of Search ................................ 260/465 G

[56] References Cited
OTHER PUBLICATIONS
Elslager et al: J. Med. Chem., Vol. 13, No. 3, pp. 542–544 (1970).

*Primary Examiner*—Lewis Gotts
*Assistant Examiner*—Dolph H. Torrence
*Attorney, Agent, or Firm*—Burgess, Dinklage & Sprung

[57] ABSTRACT

Benzonitrile derivatives having the formula:

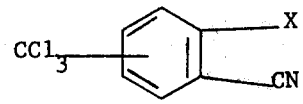

wherein X is Cl or $CCl_3$, are prepared by reacting dimethyl benzonitriles having the formula:

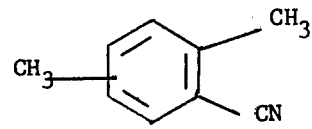

with chlorine at temperatures of from 20° to 200°C, optionally in the presence of UV-irradiation to form bis-(trichloromethyl)-benzonitriles which are optionally chlorinated, if necessary after intermediate isolation, in a second reaction stage at temperatures of from 200° to 280°C until the elimination of carbon tetrachloride is over.

8 Claims, No Drawings

2-CHLORO-TRICHLORO-BENZONITRILES

This invention relates to 2-chlorotrichloromethyl benzonitriles and to bis-(trichloromethyl)-benzonitriles which can be isolated as an intermediate stage. The invention also relates to a process for producing these new compounds.

SUMMARY

It has been found that 2-chlorotrichloromethyl benzonitriles and bis-(trichloromethyl)-benzonitriles can readily be obtained on a large scale by reacting dimethyl benzonitriles corresponding to the general formula (I):

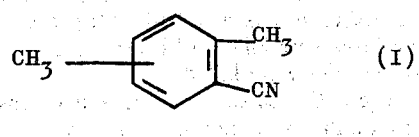

with chlorine at a temperature of from 20° to 200°C, optionally under ultraviolet irradiation, to form bis-(trichloromethyl)-benzonitriles and optionally chlorinating the bis-(trichloromethyl)-benzonitriles thus obtained, optionally after intermediate isolation, in a second reaction stage at a temperature of from 200° to 280°C until the liberation of carbon tetrachloride is over.

The compounds obtainable by the process according to the invention correspond to the general formula (II):

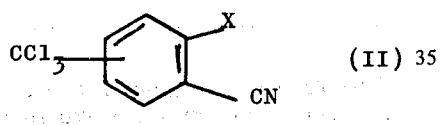

in which X represents Cl or $CCl_3$.

These compounds are new; the compounds in which X represents $CCl_3$ occur as an intermediate stage on completion of the first stage of the reaction and can be isolated.

DESCRIPTION

The process according to the invention is illustrated by the following equation:

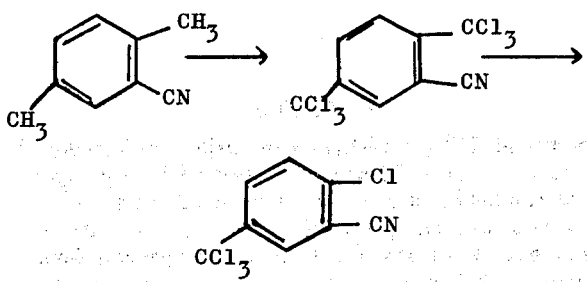

The starting compounds used for the process, namely the dimethyl benzonitriles, are readily obtainable. Any isomeric dimethyl benzonitriles can readily be obtained, either by subjecting the trimethylbenzenes to oxidation with ammonia or by subjecting the xylidines to Sandmeyer's reaction. The following are mentioned as examples of the starting compounds: 2,4-dimethyl benzonitrile, 2,5-dimethyl benzonitrile and 2,6-dimethyl benzonitrile.

The 2-chlorotrichloromethyl benzonitriles are preferably obtained by chlorination in stages. To this end, gaseous chlorine is initially introduced in to the dimethyl benzonitriles under the condition of a side-chain chlorination, optionally under UV-irradiation, at a temperature of from 20° to 200°C, preferably from 70° to 190°C. The end products of this reaction stage are the corresponding new bistrichloromethyl benzonitriles. They can be purified either by distillation or by recrystallization. In most cases, however, they are sufficiently pure so that further processing can be carried out in a second stage in which the $CCl_3$ group in the ortho position to the nitrile group is eliminated and a chlorine atom introduced into this position by further reaction with chlorine at an elevated temperature (200°– 280 °C, preferably 230° – 260°C). Chlorolytic splitting has been repeatedly described in the aliphatic series. A summary can be found in Houben-Weyl, 4th Edition, Vol. V/3, pages 1,013 – 1.017.

The selective chlorolytic splitting of an alkyl side chain linked to the aromatic ring of a substituted aromatic compound, which is what the preferred process represents, is unknown. It is surprising that the $CCl_3$ group in the ortho position is split off so distinctly preferentially with respect to the second $CCl_3$ group on the benzene nucleus or the nitrile group, irrespective of the position relative to the nitrile group of the second $CCl_3$ group.

The end products of the process according to the invention are used as intermediate products for the production of corresponding trifluoromethyl chlorobenzonitriles. The 2-chlorotrichloromethyl benzonitriles and bis-(trichloromethyl)-benzonitriles obtainable by the process can be used as herbicides and also for controlling *Aedes aegypti* and Drosophila. Their herbicidal activity is illustrated in the following example:

Pre-emergence test

Solvent: 5 parts by weight of acetone
Emulsifier: 1 part by weight of alkylaryl polyglycol ether.

In order to make up a suitable active substance preparation, 1 part by weight of the active substance is mixed with the specified quantity of solvent, the specified quantity of emulsifier is added and the concentrate is diluted with water to the required concentration.

Seeds of the test plants were sown in normal soil and watered with the active substance preparation after 24 hours. The quantity of water per unit area is best kept constant. The concentration of the active substance in the preparation is unimportant, the only crucial factor being the quantity in which the active substance is applied per unit area. After 3 weeks, the degree to which the test plants were damaged was determined and given marks, from 0 to 5, which have the following meaning:

0 = no effect;
1 = slight damage or delay in growth;
2 = distinct damage or inhibition of growth;
3 = serious damage, and only defective development or only 50 percent emergence;
4 = plants partly destroyed after gemination, or only showing 25 percent emergence;
5 = plants completely killed or not emerging.

The active substances, the quantities applied, and the results are set out in Table (I):

Table (I)

| Compound | Quantity of active substance, applied kg/ha | Chenopodium | Echino chloa | Sinapis |
|---|---|---|---|---|
| 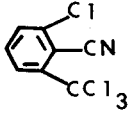 | 40 | 5 | 5 | 5 |

The other new compounds obtainable by the process according to the invention also show comparable herbicidal activity.

The ability of the new compounds to control *Aedes aegypti* is illustrated in the following example:

$LT_{100}$-test for dipters

Test parasites: *Aedes aegypti*
Solvent: acetone 2 parts by weight of the active substance are taken up in 1000 parts by volume of solvent. The solution thus obtained is diluted with further solvent to the required relatively low concentrations.

2.5 ml of the active substance solution are pipetted into a Petri dish. On the bottom of the Petri dish is a filter paper with a diameter of approximately 9.5 cm. The Petri dish remains open until the solvent has completely evaporated. The quantity of the active substance per m² of filter paper differs according to the concentration of the active substance solution. Approximately 25 test parasites are then introduced into the Petri dish and covered with a glass lid.

The condition of the test parasites is continuously checked. The time required to obtain 100 % mortality is determined.

The test parasites, active substances, active substance concentrations and times required to produce 100 % mortality are shown in Table (II):

Table (II)

| Active substances | Test parasites | Active substance concentration of the solution in % | $LT_{100}$ |
|---|---|---|---|
| 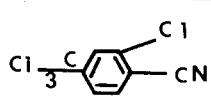 | Aedes aegypti | 0.2 | 60 mins. |
| | | 0.02 | 60 mins. |

The other new compounds obtainable by the process according to the invention also show a comparable effect.

The ability of the new compounds to control Drosophila is illustrated in the following example:

Drosophila test

Solvent: 3 parts by weight of alkylaryl polyglycol ether
Emulsifier: 1 part by weight of dimethyl formamide.

To make up a suitable active substance preparation, 1 part by weight of the active substance is mixed with the specified quantity of solvent containing the specified quantity of emulsifier, and the concentrate is diluted with water to the required concentration.

1 cc of the active substance preparation is pipetted onto a 7 cm diameter disc of filter paper. While still wet the filter paper is placed on a glass containing 50 dew flies (Drosophila melanogaster) and covered with a glass plate.

The mortality rate as a percentage is determined after the periods specified. 100 percent means that all the flies were killed, whilst 0 percent means that none of the flies were killed.

The active substances, the active substance concentration the evaluation times and the percentage mortality are shown in Table (III).

Table (III)

| Active substance | Active substances concentration in % | Mortality in % after 1 day |
|---|---|---|
| 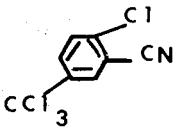 | 0.1 | 100 |
| | 0.01 | 100 |

The other new compounds obtainable by the process according to the invention also show a comparable effect.

The process is illustrated in the following Examples:

EXAMPLE 1

450 g of 2,5-dimethyl benzonitrile are introduced into a 3-necked flask with a chlorine inlet pipe and chlorinated in the presence of UV irradiation at a temperature increasing slowly from 100° to 200°C, until no more chlorine is absorbed. The reaction product is then worked up by distillation. After a few first runnings, 2,5-bis-(trichloromethyl)-benzonitrile distils over in a yield of 1080 g (87.5 percent of the theoretical), b.p. 195° – 200°C/12 Torr, m.p. 112° – 113°C.

776 g of 2,5-bis-(trichloromethyl)-benzonitrile are treated with chlorine in the presence of UV irradiation at a temperature rising from 200° to 260°C (1 to 1.5 hours). Carbon tetachloride is continuously distilled off. When the liberation of carbon tetrachloride is over, the reaction product is worked up by distillation.

2-chloro-5-trichloromethyl benzonitrile is obtained in a yield of 458 g (78 percent), b.p. 171° – 172°C/12 Torr, m.p. 66° – 68°C.

EXAMPLE 2

245 g of 2,4-dimethylbenzonitrile are introduced into a chlorination apparatus and treated with gaseous chlorine in the presence of UV irradiation at a temperature rising from 50° to 195°C until no more chlorine is absorbed.

When the absorption of chlorine is over, the reaction product is distilled. After some first runnings, 2,4-bis-(trichloromethyl)-benzonitrile is obtained in a yield of 520 g, b.p. 175°C/3 Torr, m.p. 76° – 78°C.

500 g of 2,4-bis-(trichloromethyl)-benzonitrile are chlorinated at a temperature rising slowly from 200° to 270°C. 358 g of distillate are obtained after a coarse distillation. According to a gas chromatogram, the liquid has the following composition:

76 percent of 2-chloro-4-trichloromethyl benzonitrile,
13 percent of 2,4-dichlorobenzonitrile, and
5 percent of unchanged starting material (rest unknown components).

The 2-chloro-4-trichloromethyl benzonitrile can readily be isolated from the crude product by fractional distillation. b.p. 173°–176°C/14 Torr, m.p. 68° – 70°C.

EXAMPLE 3

2,6-bis-(trichloromethyl)-benzonitrile, m.p. 218° – 220°C, and 2-chloro-6-trichloromethyl benzonitrile, b.p. 146° – 148°C/12 Torr, m.p. 121° – 122°C, are obtained in the same way as described in Example 1.

EXAMPLE 4 a. 1000 g of 2,5-dimethyl benzonitrile are initially introduced into a glass flask equipped with a stirring mechanism, a gas inlet pipe, an ascending condenser, which is kept at about 50°C, and a following descending condenser with a cooling water temperature of from 10° to 50°C, and initially chlorinated under UV-irradiation, beginning at 70°C. The temperature is increased to 195°C commensurate with the absorption of chlorine, and chlorination is continued at this temperature until there is no further absorption of chlorine or elimination of hydrogen chloride. The temperature is then increased to 240°C over 20 to 50 minutes and then to 260°C over another 4 hours, the introduction of chlorine being continued. At the end of this time, the elimination of carbon tetrachloride which can be followed from the descending condenser, is over. Distillation gives 67 g of first runnings of b.p. 150° – 155°C/12 Torr, m.p. 125° – 127°C, corresponding to 2,5-dichlorobenzonitrile (A), 1950 g of 2-chloro-5-trichloromethyl benzonitrile (B) and 450 g of predominantly 2,5-bis-(trichloromethyl)-benzonitrile (C). This corresponds to a yield of 73.5 percent of (B) and 12.8 percent of (C), which can be used for another chlorolysis reaction.

b. If the reaction described in (a) is carried out in the absence of ultraviolet irradiation, the first stage carried out at the upper end of the temperature range (more rapid heating than in (a) from 130° to 195°C) and if the further procedure is then as in (a), the result described there is obtained.

What we claim is:

1. Benzonitrile derivative having the formula:

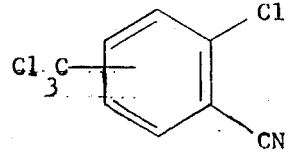

2. Compound of claim 1 selected from the group of 2-chloro-4-trichloromethyl-benzonitrile; 2-chloro-5-trichloromethyl-benzonitrile; and 2-chloro-6-trichloromethyl-benzonitrile.

3. Process for preparing a 2-chloro-trichloromethyl-benzonitrile which comprises the steps of
   i. reacting a dimethyl benzonitrile having the formula

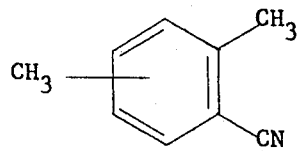

in a first reaction stage with chlorine at a temperature in the range of 20° to 200°C, forming bis-(trichloromethyl)-benzonitrile; and
   ii. further chlorinating said bis-(trichloromethyl)-benzonitrile in a second reaction stage at a temperature in the range of from 200° to 280°C until the elimination of carbon tetrachloride is over, forming a 2-chloro-trichloromethylbenzonitrile.

4. Process of claim 3 wherein the chlorination in the first stage is carried out in the presence of ultraviolet irradiation.

5. Process of claim 3 wherein the bis-(trichloromethyl)-benzonitrile formed during the first reaction stage is isolated as an intermediate before undergoing the second reaction stage.

6. Process of claim 3 wherein the first stage chlorination is carried out at a temperature in the range of from 70° to 190°C.

7. Process of claim 3 wherein chlorination is carried out in the second stage at a temperature in the range 230° to 260°C.

8. Process of claim 3 wherein both stages of the reaction are carried out in the presence of ultraviolet irradiation.

* * * * *